(12) United States Patent
Nicolosi et al.

(10) Patent No.: US 6,987,205 B2
(45) Date of Patent: Jan. 17, 2006

(54) PROCESS FOR THE PREPARATION OF 1-(3-TRIFLUOROMEHYLPHENYL)-PROPAN-2-OL ENANTIOMERS

(75) Inventors: Giovanni Nicolosi, Valverde (IT); Sebastiano Mangiafico, Noto (IT); Nicola D'Antona, Valverde (IT)

(73) Assignees: Fidia Farmaceutici S.p.A., Abano Terme (IT); Consiglio Nazionale Delle Ricerche, Rome (IT)

( * ) Notice: Subject to any disclaimer, the term of this patent is extended or adjusted under 35 U.S.C. 154(b) by 166 days.

(21) Appl. No.: 10/466,056

(22) PCT Filed: Jan. 10, 2002

(86) PCT No.: PCT/EP02/00182

§ 371 (c)(1), (2), (4) Date: Aug. 7, 2003

(87) PCT Pub. No.: WO02/055724

PCT Pub. Date: Jul. 18, 2002

(65) Prior Publication Data

US 2005/0176119 A1    Aug. 11, 2005

(30) Foreign Application Priority Data

Jan. 12, 2001    (IT) .............................. MI01A0047

(51) Int. Cl.
C07L 33/46    (2006.01)

(52) U.S. Cl. ..................................... 568/812; 435/156

(58) Field of Classification Search ................ 568/812; 435/156

See application file for complete search history.

(56) References Cited

U.S. PATENT DOCUMENTS 4,963,492 A * 10/1990 Keller et al. ................. 435/280
5,756,321 A * 5/1998 Schudok et al. ............ 435/123

FOREIGN PATENT DOCUMENTS

EP    0 441 160 A    8/1991

OTHER PUBLICATIONS

"Kirk-Orthmer Encyclopedia of Chemical Technology," 4th Ed., vol. 9, pp. 672-714 (1994).*
Garca-Urdiales E. et al., Tetrahedron: Asymmetry, Elsevier Science vol. 11, No. 7, Apr. 2000, pp. 1459-1463.
Database CA Online, Chemical Abstracts Service, Columbus Ohio, US; Goument, B. et al., retrieved from STN Database accession No. 120:244208, XP002195662, abstract & Bull. Soc. Chim. Fr. (1993), 130(4), 450-8.
Kawasaki M. et al., Tetrahedron: Asymmetry, Elsevier Science Publishers, Amsterdam, NL, vol. 12, No. 4, Mar. 19, 2001, pp. 585-596, XP004234157.

* cited by examiner

Primary Examiner—Michael L. Shippen
(74) Attorney, Agent, or Firm—Birch, Stewart, Kolasch & Birch, PLL

(57) ABSTRACT

A process for the preparation of 1-(3-trifluoromethylphenyl)-propan-2-ol enantiomersthrough enzymatic resolution by a lipase.

11 Claims, No Drawings

PROCESS FOR THE PREPARATION OF 1-(3-TRIFLUOROMEHYLPHENYL)-PROPAN-2-OL ENANTIOMERS

This application is the national phase under 35 U.S.C. § 371 of PCT International Application No. PCT/EP02/00182 which has an International filing date of Jan. 10, 2002, which designated the United States of America.

The present invention relates to a process for the preparation of 1-(3-trifluoromethylphenyl)-propan-2-ol enantiomers through enzymatic resolution by a lipase.

1-(3-Trifluoromethylphenyl)-propan-2-ol enantiomers are useful intermediates for the preparation of the enantiomers of fenfluramine, a known medicament with anorectic activity used in the treatment of obesity. In particular, S-fenfluramine, which is considered the more active enantiomer, or eutomer, (Grice et al. Clin. Exp. Pharmacol. Physiol. 1998, 25, 621–23), can be obtained by tosylation of R-(−)1-(3-trifluoromethylphenyl)-propan-2-ol and subsequent reaction with ethylamine.

A process for the separation of R,S-fenfluramine enantiomers by selective crystallization has been described [Morehead AT jr. et al., Enantiomer 1996, 1, 63–8]. The kinetic resolution of the amine precursor of fenfluramine by lipase-catalyzed enantioselective acylation has also been effected [Garcia-Urdiales et al., Tetrahedron: Asymmetry, 2000. 11, 1459–63]. Both procedures however involve the problem of the recycle of the undesired enantiomer.

EP-A-441160 discloses a process for the preparation of the two fenfluramine isomers, which uses as an intermediate the chiral alcohol obtained by reducing (3-trifluoromethylphenyl)acetone with beer yeast. Said process provides only one of the two enantiomeric alcohols, as a product of the enantioselective reduction, but has the drawback of requiring a high number of steps, so that the final yield in S-fenfluramine is rather low.

It is therefore necessary to develop a simple, advantageous method for the preparation of fenfluramine precursors in enantiopure form.

Said problem is solved by the process of the invention, which makes use of lipase biocatalysis in an organic solvent to obtain both enantiopure forms of 1-(3-trifluoromethylphenyl)-propan-2-ol (1) enantiomers in high yields.

It has, in fact, been found that some lipases are capable of catalyzing the esterification of (1) with high enantioselectivity, to yield the ester (2) with configuration R and the alcohol (1) with configuration S.

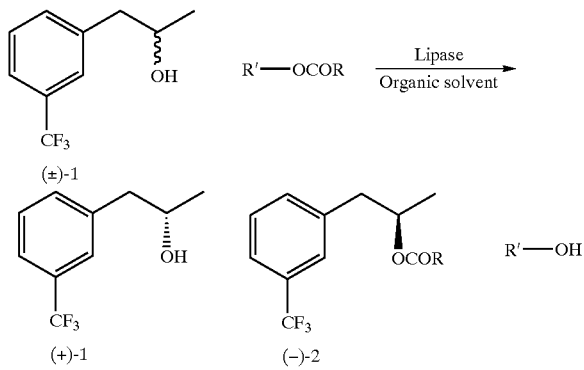

Said lipases are also capable of enantioselectively catalyzing the alcoholysis of 1-(3-trifluoromethylphenyl)-propan-2-ol racemic ester (2), to give the alcohol (1) with configuration R and the ester (2) with configuration S.

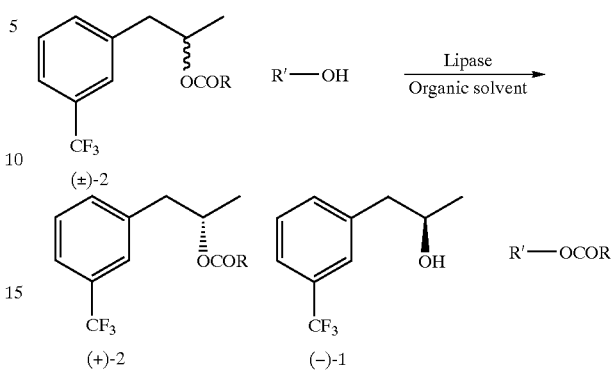

Therefore, the invention provides a process for the preparation of 1-(3-trifluoromethylphenyl)-propan-2-ol enantiomers, which process comprises the esterification of racemic 1-(3-trifluoromethylphenyl)-propan-2-ol with an acylating agent or the alcoholysis of 1-(3-trifluoromethylphenyl)-propan-2-ol esters of formula

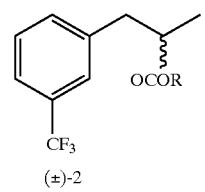

wherein R is alkyl or $C_1$–$C_8$ alkenyl or benzoyl, in the presence of a lipase and the separation of the unreacted S-(+) 1-( 3-trifluoromethylphenyl)-propan-2-ol or of the corresponding ester respectively from R-(−) 1-(3-trifluoromethylphenyl)-propan-2-ol ester or from R-(−) 1-(3-trifluoromethylphenyl)-propan-2-ol resulting from the esterification or lipase-catalyzed hydrolysis/alcoholysis reactions.

In the case of the resolution through esterification, the acylating agent is preferably selected from the vinyl or isopropenyl alcohols esters, in particular vinyl acetate, vinyl propionate, isopropenyl acetate, vinyl benzoate.

The lipases for use in the process of the invention are commercially available and derive from microorganisms such as *Candida antarctica, Mucor miehei* or *Pseudomonas cepacia*.

The esterification reaction is carried out in an organic apolar solvent compatible with the lipase, such as pentane, hexane, heptane, octane, dichloromethane, diethyl ether, diisopropyl ether, t-butyl methyl ether, preferably hexane, at a temperature ranging from 20 to 70° C., for times ranging approximately from 30 min to 10 hours.

In the case of resolution through alcoholysis, the same lipases can be used as well as the same conditions and solvents as described for the esterification, in the presence of a straight alkyl alcohol, preferably n-butanol. Acetic, propionic, benzoic esters and the like, preferably the acetic ester, can be used as racemic esters.

Both in the esterification and in the alcoholysis, the lipases selectively recognize the isomer with configuration R, which can be transformed into ester or hydrolyzed with enantiomeric purity above 98%. The separation of the reaction products is carried out with known procedures.

Racemic 1-(3-trifluoromethylphenyl)-propan-2-ol can be obtained by reduction of 1-(3-trifluoromethylphenyl)acetone, preferably by reaction with lithium aluminium hydride in ethyl ether.

The process of the invention can also be used for the optical resolution of 1-(phenyl)-propan-2-ol or of derivatives substituted at the phenyl ring with hydroxy or methoxy groups, in particular at the meta and para positions.

The following examples illustrate the invention in greater detail.

EXAMPLE 1

Preparation of (R)-1-(3-trifluoromethylphenyl)-propan-2-ol, (−)-(1) and of (S)-1-(3-trifluoromethylphenyl)-propan-2-ol, (+)-(1), by esterification.

One gram of 1-(3-trifluoromethylphenyl)-propan-2-ol, (±)-(1), is dissolved in 100 ml of hexane, then is added with 0.5 g of Novozym (lipase from *Candida antarctica*) and 1 ml of vinyl acetate. The suspension is then incubated at 45° C. in a rotating stirrer (300 rpm). After 1 h, when the reaction mixture contains only two compounds in 1:1 ratio, the reaction is stopped and the solvent is distilled off under vacuum. The resulting residue is subjected to chromatographic separation on silica gel, eluting with ethyl ether/petroleum ether gradient, to yield 0.627 g of (R)-1-(3-trifluoromethylphenyl)-propan-2-ol acetic ester, (−)-(2), (52% yield, 92% ee) and (S)-1-(3-trifluoromethylphenyl)-propan-2-ol, (+)-(1), 0.470 g (47% yield, >98% ee). The (−)-(2) ester is dissolved in 50 ml of hexane containing 1.5 ml of butanol and added with 0.5 g of Novozym. The suspension is then incubated at 45° C. in a rotating stirrer (300 rpm). After 5 h, the reaction is stopped to yield (R)-1-(3-trifluoromethylphenyl)-propan-2-ol, (−)-(1), 0.488 g (94% yield, >98% ee).

EXAMPLE 2

Preparation of (R)-1-(3-trifluoromethylphenyl)-propan-2-ol, (−)-(1) and of (s-1-(3-trifluoromethylphenyl)-propan-2-ol, (+)-(1), by alcoholysis.

One gram of 1-(3-trifluoromethylphenyl)-propan-2-ol acetic ester (±)-2 is dissolved in 100 ml of hexane, which is added with 0.5 g of Novozym (lipase from *Candida antarctica*) and 1 ml of butanol. The suspension is then incubated at 45° C. in a rotating stirrer (300 rpm). After 6 h, when the reaction mixture contains only two reaction products in a 1:1 ratio, the reaction is stopped and the solvent is distilled off under vacuum. The resulting residue is subjected to chromatographic separation on silica gel eluting with petroleum ether/ethyl ether gradient, to yield 0.480 g of (S)-1-( 3-trifluoromethylphenyl)-propan-2-ol acetic ester, (+)-(2) (48% yield, >98% ee) and (R)-1-(3-trifluoromethylphenyl)-propan-2-ol (−)-(1), 0.420 g (51% yield, 96% ee).

What is claimed is:

1. A process for the preparation of 1-(3-trifluoromethylphenyl)-propan-2-ol enantiomers, said method comprising the steps of:
providing a lipase derived from *Candida antarctica*, *Mucor miehei*, or *Pseudomonas cepacia*;
esterifying racemic 1-(3-trifluoromethylphenyl)-propan-2-ol with an acylating agent in the presence of said lipase or performing an alcoholysis of 1-(3-trifluoromethylphenyl)-propan-2-ol esters of the following formula in the presence of said lipase:

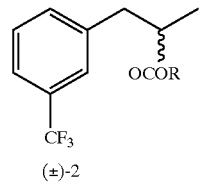

(±)-2 wherein R is alkyl or $C_1$–$C_8$ alkenyl or benzoyl; and
separating unreacted S-(+)1-(3-trifluoromethylphenyl)-propan-2-ol or the corresponding ester respectively from the R-(−)1-(3-trifluoromethylphenyl)-propan-2ol ester or from the R-(−)1-(3-trifluoromethylphenyl)-propan-2-ol resulting from the lipase-catalyzed esterification or alcoholysis reaction.

2. The process as claimed in claim 1, which comprises the esterification of racemic 1-(3-trifluoromethylphenyl)-propan-2-ol with an acylating agent in the presence of a lipase and the subsequent separation of S-(+)1-(3-trifluoromethylphenyl)-propan-2-ol from the R-(−) 1-(3-trifluoromethylphenyl)-propan-2-ol ester.

3. The process as claimed in claim 2, wherein the acylating agent is a vinyl ester or an isopropenyl alcohol ester.

4. The process as claimed in claim 3, wherein the acylating agent is selected from the group consisting of vinyl acetate, isopropenyl acetate, and vinyl benzoate.

5. The process as claimed in any one of claims 2 to 4, wherein the esterification reaction is carried out in hexane.

6. The process as claimed in claim 1, said method comprising:
providing a lipase derived from *Candida Antarctica*, *Mucor miehei*, or *Pseudomonas cepacia*;
performing an alcoholysis of 1-(3-trifluoromethylphenyl)-propan-2-ol esters of the following formula in the presence of said lipase and a straight $C_2$–$C_6$ alkyl alcohol:

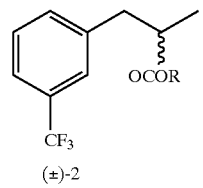

(±)-2 wherein R is alkyl or $C_1$–$C_8$ alkenyl or benzoyl,
separating unreacted S-(+)1-(3-trifluoromethylphenyl)-propan-2-ol ester from R-(−)1-(3-trifluoromethylphenyl)-propan-2-ol.

7. The process as claimed in claim 6, wherein the alkyl alcohol is n-butanol.

8. The process as claimed in claim 6 or 7, wherein R is methyl.

9. The process as claimed in claim 6 or 7, wherein the alcoholysis is carried out in hexane.

10. The process as claimed in claim 1 or 6, wherein the lipase is derived from *Candida antarctica*.

11. The process as claimed in claim 8, wherein the alcoholysis is carried out in hexane.

* * * * *